(12) United States Patent
Hirayu

(10) Patent No.: US 10,357,222 B2
(45) Date of Patent: Jul. 23, 2019

(54) X-RAY DIAGNOSTIC IMAGING APPARATUS, MONITORING SERVER AND ANOMALY DETECTION METHOD

(71) Applicant: Hitachi, Ltd., Tokyo (JP)

(72) Inventor: Takeshi Hirayu, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 197 days.

(21) Appl. No.: 15/529,108

(22) PCT Filed: Dec. 24, 2015

(86) PCT No.: PCT/JP2015/085924
§ 371 (c)(1),
(2) Date: May 24, 2017

(87) PCT Pub. No.: WO2016/104557
PCT Pub. Date: Jun. 30, 2016

(65) Prior Publication Data
US 2017/0281118 A1   Oct. 5, 2017

(30) Foreign Application Priority Data

Dec. 26, 2014 (JP) .................................. 2014-263881

(51) Int. Cl.
*A61B 6/00* (2006.01)
*A61B 6/03* (2006.01)
(Continued)

(52) U.S. Cl.
CPC .............. *A61B 6/586* (2013.01); *A61B 6/03* (2013.01); *A61B 6/032* (2013.01); *A61B 6/0407* (2013.01);
(Continued)

(58) Field of Classification Search
CPC ................................................... A61B 6/4021
See application file for complete search history.

(56) References Cited

U.S. PATENT DOCUMENTS

2010/0303202 A1* 12/2010 Ren .................... A61B 6/025
378/62
2011/0051895 A1* 3/2011 Vogtmeier ............ A61B 6/032
378/92
(Continued)

FOREIGN PATENT DOCUMENTS

JP     2005095651 A     4/2005
JP     2006340954 A    12/2006
(Continued)

OTHER PUBLICATIONS

International Search Report received for PCT Patent Application No. PCT/JP2015/085924, dated Mar. 26, 2016, 1 page.

*Primary Examiner* — Hoon K Song

(57) ABSTRACT

In order to provide an X-ray diagnostic imaging apparatus which can detect anomalies caused by factors other than wearing of a bearing of an X-ray tube, according to the present invention, there is provided an X-ray diagnostic imaging apparatus including an X-ray tube that irradiates an object with X-rays, an X-ray detector that detects X-rays having been transmitted through the object, an image creation unit that creates a medical image of the object on the basis of the output of the X-ray detector, a change amount measurement unit that measures a change amount of an X-ray focal point which is an X-ray generation point of the X-ray tube, and an anomaly detection unit that detects an anomaly in the X-ray tube on the basis of whether or not the change amount falls within a predetermined normal change range.

14 Claims, 14 Drawing Sheets

(51) Int. Cl.
    *A61B 6/04*         (2006.01)
    *H05G 1/52*        (2006.01)
    *H01J 35/14*      (2006.01)

(52) U.S. Cl.
    CPC .............. *A61B 6/40* (2013.01); *A61B 6/4435* (2013.01); *A61B 6/461* (2013.01); *A61B 6/5205* (2013.01); *A61B 6/54* (2013.01); *H05G 1/52* (2013.01); *A61B 6/4021* (2013.01); *H01J 35/14* (2013.01)

(56) References Cited

U.S. PATENT DOCUMENTS

| | | | |
|---|---|---|---|
| 2012/0163530 A1* | 6/2012 | Sainath | A61B 6/027 378/5 |
| 2017/0105687 A1* | 4/2017 | Tkaczyk | A61B 6/4021 |
| 2017/0319149 A1* | 11/2017 | Koehler | A61B 6/032 |

FOREIGN PATENT DOCUMENTS

| | | |
|---|---|---|
| JP | 2011045626 A | 3/2011 |
| WO | 2012046813 A1 | 4/2012 |

\* cited by examiner

FIG.4
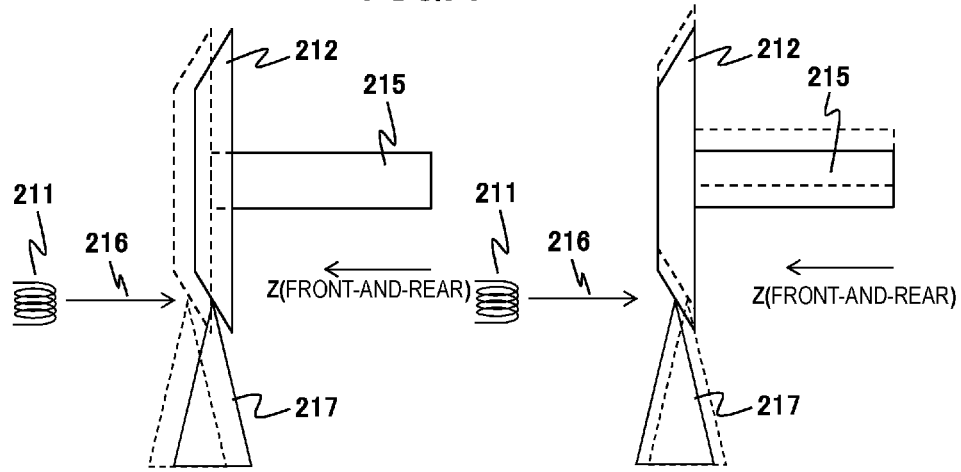
(a)  (b)
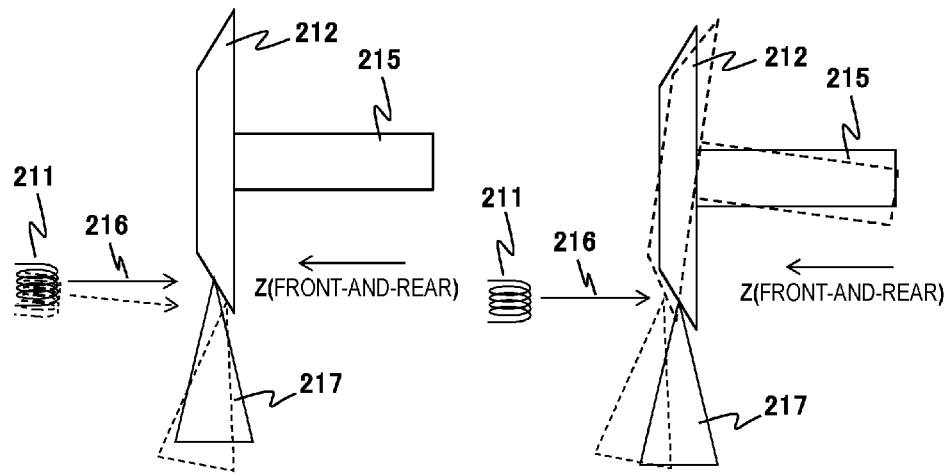
(c)  (d)

FIG.5
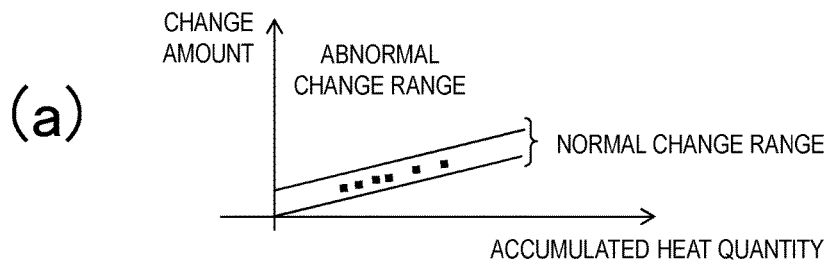
(a)
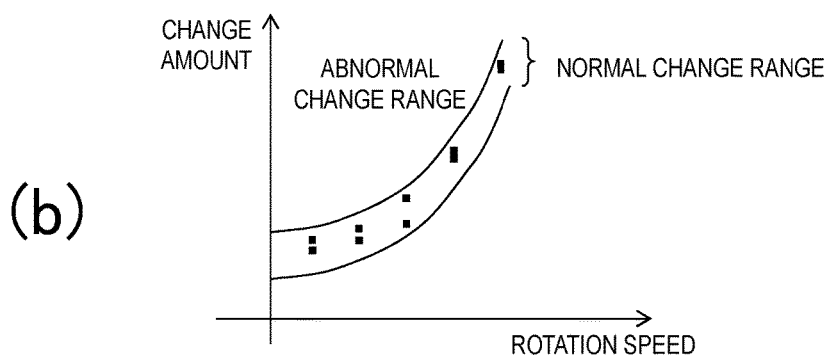
(b)
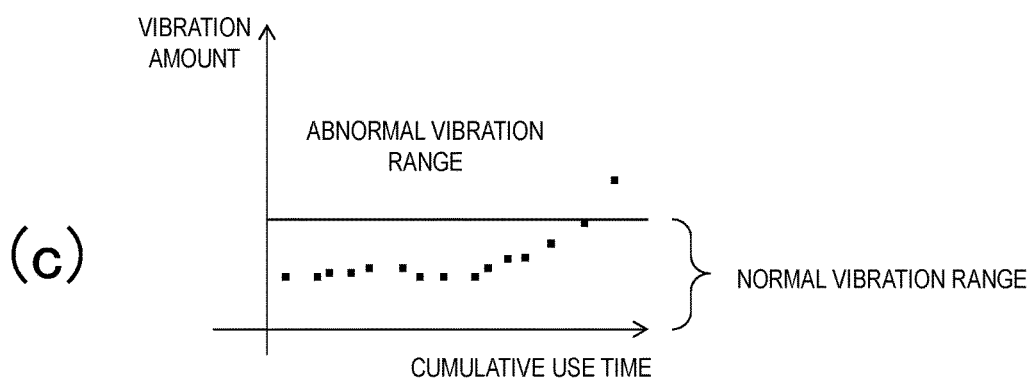
(c)

X-RAY DIAGNOSTIC IMAGING APPARATUS, MONITORING SERVER AND ANOMALY DETECTION METHOD

CROSS-REFERENCE TO RELATED APPLICATIONS

This application is a national phase claiming the benefit of and priority to International Patent Application No. PCT/JP2015/085924, entitled "X-RAY DIAGNOSTIC IMAGING DEVICE, MONITORING SERVER, AND ANOMALY DETECTION METHOD", filed Dec. 24, 2015, which claims priority to Japanese Patent Application No. 2014-263881, filed Dec. 26, 2014 which are hereby incorporated by reference in their entireties.

TECHNICAL FIELD

The present invention relates to an X-ray diagnostic imaging apparatus such as an X-ray computed tomography (CT) apparatus, and particularly to a technique of detecting an anomaly in an X-ray tube.

BACKGROUND ART

An X-ray diagnostic imaging apparatus is an apparatus which irradiates an object with X-rays, detects a dose of X-rays having been transmitted through the object, and thus creates and displays a medical image of the object, and the created medical image is used to diagnose the object. An X-ray tube which is an X-ray source of the X-ray diagnostic imaging apparatus is a device which accelerates electron beams emitted from a cathode with a voltage of a hundred and several tens of kV, and generates X-rays due to bremsstrahlung when the electron beams collide with an anode. Since the electron beams colliding with the anode heat the anode, a rotary anode type X-ray tube in which an anode is rotated in order to distribute heat locations is used for a lot of X-ray diagnostic imaging apparatuses.

In the X-ray tube, an anomaly may occur due to various factors, for example, wearing of a bearing which rotatably supports a rotation axis of the anode, and thus it is desirable to detect this anomaly before occurring. PTL 1 discloses a technique of detecting vibration of an anode and detecting an anomaly state of an X-ray tube on the basis of an AC component with a predetermined bandwidth included in a detection signal.

CITATION LIST

Patent Literature

PTL 1: JP-A-2002-280195

SUMMARY OF INVENTION

Technical Problem

However, in PTL 1, it is possible to detect an anomaly caused by wearing of a bearing supporting a rotation axis of the anode, but there is no consideration of anomalies caused by factors other than the wearing of the bearing.

Therefore, a purpose of the present invention is to provide an X-ray diagnostic imaging apparatus which can detect anomalies caused by factors other than wearing of a bearing of an X-ray tube.

Solution to Problem

In order to achieve the above-described purpose, the present invention is characterized in that a change amount of an X-ray focal point which is an X-ray generation point of the X-ray tube is measured, and an anomaly in the X-ray tube is detected on the basis of whether or not the change amount of the X-ray focal point falls within a predetermined normal change range.

Specifically, according to the present invention, there is provided an X-ray diagnostic imaging apparatus including an X-ray tube that irradiates an object with X-rays; an X-ray detector that detects X-rays having been transmitted through the object; an image creation unit that creates a medical image of the object on the basis of the output of the X-ray detector; a change amount measurement unit that measures a change amount of an X-ray focal point which is an X-ray generation point of the X-ray tube; and an anomaly detection unit that detects an anomaly in the X-ray tube on the basis of whether or not the change amount falls within a predetermined normal change range, in which the anomaly detection unit includes a comparison unit that compares the change amount with the normal change range correlated with scanning conditions when the change amount is measured, so as to determine the presence or absence of an anomaly in the X-ray tube.

According to the present invention, there is provided a monitoring server connected to the X-ray diagnostic imaging apparatus via a network, in which the monitoring server receives data regarding the change amount or data regarding an output from the anomaly detection unit from the X-ray diagnostic imaging apparatus, and collectively manages the data.

According to the present invention, there is provided an anomaly detection method of detecting an anomaly in an X-ray diagnostic imaging apparatus including an X-ray tube that irradiates an object with X-rays, an X-ray detector that detects X-rays having been transmitted through the object, and an image creation unit that creates a medical image of the object on the basis of the output of the X-ray detector, the method including a measurement step of measuring a change amount of an X-ray focal point which is an X-ray generation point of the X-ray tube; and an anomaly detection step of detecting an anomaly in the X-ray tube on the basis of whether or not the change amount falls within a predetermined normal change range, in which the anomaly detection step includes a comparison step of comparing the change amount with the normal change range correlated with scanning conditions when the change amount is measured, so as to determine the presence or absence of an anomaly in the X-ray tube.

Advantageous Effects of Invention

According to the present invention, it is possible to provide an X-ray diagnostic imaging apparatus which can detect anomalies caused by factors other than wearing of a bearing of an X-ray tube.

BRIEF DESCRIPTION OF DRAWINGS

FIG. 4 is a diagram illustrating a change in the X-ray focal point.

FIG. 5 is a diagram for explaining a normal change range of a change amount of the X-ray focal point and a normal vibration range of a vibration amount.

DESCRIPTION OF EMBODIMENTS

Figure 1:
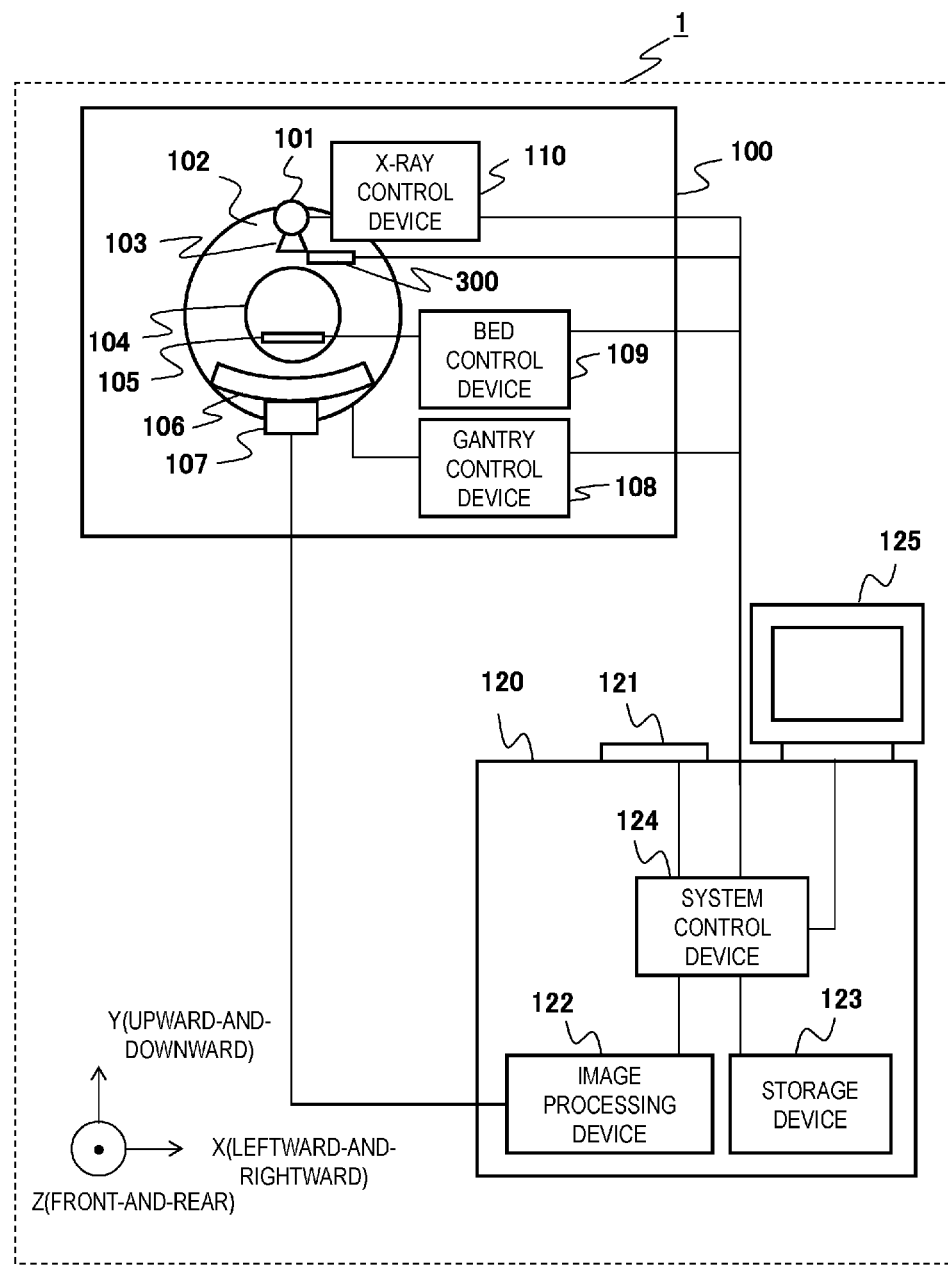
FIG. 1 is the entire configuration diagram of an X-ray CT apparatus which is an example of an X-ray diagnostic imaging apparatus according to a first embodiment.

Hereinafter, preferred embodiments of an X-ray diagnostic imaging apparatus according to the present invention will be described with reference to the drawings. In the following description and the accompanying drawings, constituent elements having the same functions and configurations are given the same reference numerals, and repeated description thereof will be omitted.

[First Embodiment]

With reference to FIG. 1, a description will be made of a summary of an X-ray CT apparatus as an example of an X-ray diagnostic imaging apparatus of the present embodiment. As illustrated in FIG. 1, an X-ray CT apparatus 1 includes a scan gantry unit 100 and an operation unit 120.

The scan gantry unit 100 includes an X-ray tube device 101, a rotation disk 102, a collimator 103, an X-ray detector 106, a data collecting device 107, a bed device 105, a gantry control device 108, a bed control device 109, an X-ray control device 110, and a change amount measurement unit 300.

The X-ray tube device 101 is a device which irradiates an object mounted on the bed device 105 with X-rays. The collimator 103 is a device which restricts a radiation field of X-rays irradiated from the X-ray tube device 101.

The rotation disk 102 is provided with an opening 104 into which the object mounted on the bed device 105 is inserted, and is also mounted with the X-ray tube device 101 and the X-ray detector 106 so as to rotate the X-ray tube device 101 and the X-ray detector 106 around the object.

The X-ray detector 106 is a device which is disposed to oppose the X-ray tube device 101, and detects X-rays having been transmitted through the object so as to measure a spatial distribution of the transmitted X-rays. The X-ray detector is formed by arranging a plurality of detection elements in a one-dimensional manner in a rotation direction of the rotation disk 102 or arranging a plurality of detection elements in a two-dimensional manner in a rotation direction and a rotation axis direction of the rotation disk 102. The data collecting device 107 is a device which collects an X-ray dose detected by the X-ray detector 106 as digital data.

The gantry control device 108 is a device which controls rotation and inclination of the rotation disk 102. The bed control device 109 is a device which controls movement of the bed device 105 in an upward-and-downward direction, a front-and-rear direction, and a leftward-and-rightward direction. The upward-and-downward direction, the front-and-rear direction, and the leftward-and-rightward direction will be respectively referred to as a Y direction, a Z direction, and an X direction as illustrated in FIG. 1 in the following description. The X-ray control device 110 is a device which controls power which is input to the X-ray tube device 101.

The change amount measurement unit 300 is a device which measures a change amount of an X-ray focal point as an X-ray generation point, particularly, a change amount in the Z direction, and is disposed at a position to which an end of X-rays irradiated to an object is incident and in a rear stage of the collimator 103. Details of the change amount measurement unit 300 will be described later with reference to FIG. 3.

The operation unit 120 includes an input device 121, an image processing device 122, a display device 125, a storage device 123, and a system control device 124.

The input device 121 is a device used to input an object name, the examination date and time, scanning conditions, alternatively, and is, specifically, a keyboard, a pointing device, a touch panel, and the like. The image processing device 122 is a device which performs a calculation process on measured data sent from the data collecting device 107 so as to reconstruct a CT image.

The display device 125 is a device which displays a CT image or the like created by the image processing device 122, and is, specifically, a cathode-ray tube (CRT), a liquid crystal display, or the like. The storage device 123 is a device which stores data collected by the data collecting device 107, and image data of a CT image created by the image processing device 122, and is, specifically, a hard disk drive (HDD), or the like.

The system control device 124 is a device which controls the above-described devices, the gantry control device 108, the bed control device 109, and the X-ray control device 110. The system control device 124 may execute a flow of a process which will be described later.

The X-ray control device 110 controls power to be input to the X-ray tube device 101 on the basis of scanning conditions which are input from the input device 121, especially, an X-ray tube voltage or an X-ray tube current, and thus the X-ray tube device 101 irradiates an object with X-rays corresponding to the scanning conditions. The X-ray detector 106 detects X-rays which are irradiated from the X-ray tube device 101 and have been transmitted through the object by using a plurality of X-ray detection elements, and thus detects a distribution of the transmitted X-rays. The rotation disk 102 is controlled by the gantry control device 108, and is rotated on the basis of scanning conditions which are input from the input device 121, especially, a rotation speed and the like. The bed device 105 is controlled by the bed control device 109, and is operated on the basis of scanning conditions which are input from the input device 121, especially, a spiral pitch and the like.

X-ray irradiation from the X-ray tube device 101 and measurement of a transmitted X-ray distribution performed by the X-ray detector 106 are repeatedly performed along with rotation of the rotation disk 102, and thus projection data from various angles is acquired. The projection data is correlated with a view indicating each angle, and a channel (ch) number and a column number which are detection element numbers of the X-ray detector 106. The acquired projection data from various angles is transmitted to the image processing device 122. The image processing device 122 performs a backprojection process on the transmitted projection data from various angles so as to reconstruct a CT image. The reconstructed CT image is displayed on the display device 125.

An example of an X-ray diagnostic imaging apparatus other than the X-ray CT apparatus 1 described with reference to FIG. 1 includes an X-ray fluoroscopic imaging apparatus. The X-ray fluoroscopic imaging apparatus is the same as the X-ray CT apparatus 1 in terms of configuration except that the rotation disk 102 and the gantry control device 108 are omitted from the X-ray CT apparatus 1.

Figure 2:
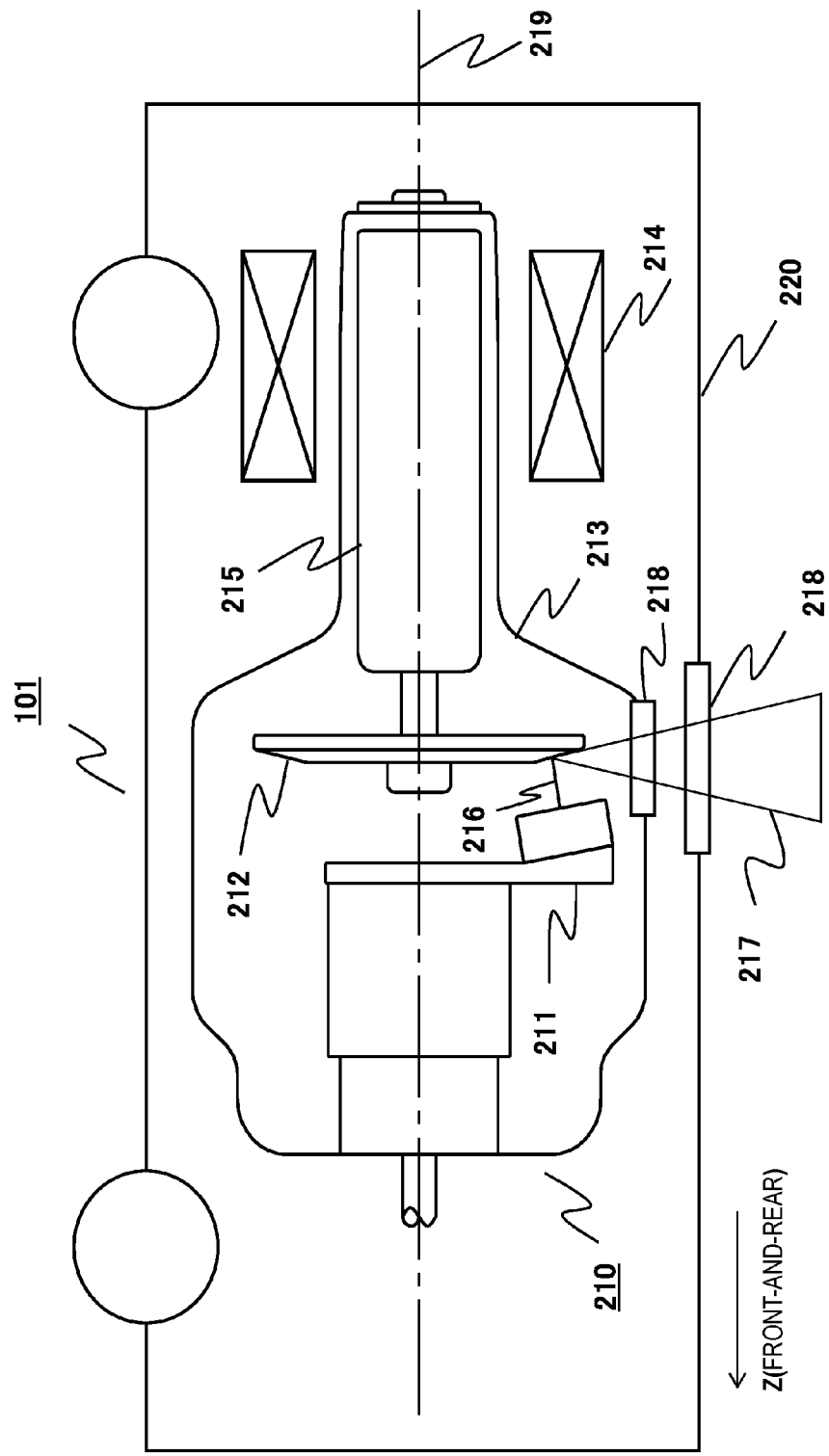
FIG. 2 is the entire configuration diagram of an X-ray tube device mounted on the X-ray diagnostic imaging apparatus.

With reference to FIG. 2, a description will be made of a configuration of the X-ray tube device 101. The X-ray tube device 101 includes an X-ray tube 210 generating X-rays and a container 220 storing the X-ray tube 210.

The X-ray tube 210 includes a cathode 211 which generates electron beams, an anode 212 to which a positive potential relative to the cathode 211 is applied, and an envelope 213 which holds the cathode 211 and the anode 212 in a vacuum atmosphere.

The cathode 211 includes a filament or a cold cathode, and a focusing electrode. The filament is obtained by winding a high melting point material such as tungsten in a coil form, and is heated when a current flows therethrough, so as to emit electrons. The cold cathode is obtained by sharply pointing a metal material such as nickel or molybdenum, and emits electrons due to field emission as a result of an electric field concentrating on a cathode surface. The focusing electrode forms a focusing electric field for focusing emitted electrons toward an X-ray focal point on the anode 212.

The filament or the cold cathode and the focusing electrode have the same potential.

The anode 212 includes a target and an anode base material. The target is made of a material such as tungsten which has a high melting point and a great atomic number. Electrons emitted from the cathode 211 collide with an X-ray focal point on the target, and thus X-rays 217 are radiated from the X-ray focal point. The anode base material is made of a material such as copper having high thermal conductivity, and holds the target. The target and the anode base material have the same potential.

The envelope 213 holds the cathode 211 and the anode 212 in a vacuum atmosphere in order to electrically insulate the cathode 211 and the anode 212 therefrom. The envelope 213 is provided with a radiation window 218 for radiating the X-rays 217 outward of the X-ray tube 210. The radiation window 218 is made of a material such as beryllium which has high X-ray transmittance and a small atomic number. The radiation window 218 may be provided on the container 220 which will be described later. A potential of the envelope 213 is a ground potential.

Electrons emitted from the cathode 211 are accelerated by a voltage applied between the cathode and the anode so as to be converted into an electron beam 216. If the electron beam 216 is focused due to a focusing electric field so as to collide with the X-ray focal point on the target, the X-rays 217 are generated from the X-ray focal point due to bremsstrahlung. The energy of the generated X-rays is determined depending on a voltage applied between the cathode and the anode, that is, a so-called tube voltage. A dose of the generated X-rays is determined depending on an amount of electrons emitted from the cathode, that is, so-called tube current and tub voltage.

A ratio in which the energy of the electron beam 216 is converted into X-rays is only about 1%, and most of the remaining energy is converted into heat. In the X-ray tube device 101 mounted in a medical X-ray diagnostic imaging apparatus, a tub voltage is a hundred and several tens of kV, and a tube current is several hundreds of mA, so that the anode 212 is heated with a heat quantity of several tens of kW.

In order to prevent the anode 212 from being overheated and melted due to this heating, the anode 212 is connected to a rotation body support 215, and is rotated with a dot chain line 219 in FIG. 2 as a rotation axis by driving the rotation body support 215.

In the following description, a rotation axis of the anode 212 will be referred to as a rotation axis 219 by using the reference numeral 219. The rotation body support 215 is driven by using a magnetic field generated by an excitation coil 214 as a rotation driving force. Since the anode 212 is rotated, and thus an X-ray focal point which is a portion with which the electron beam 216 collides is normally moved, the temperature of the X-ray focal point can be maintained to be lower than a melting point of the target, and thus it is possible to prevent the anode 212 from being overheated and melted.

The X-ray tube 210 and the excitation coil 214 are stored in the container 220. The container 220 is filled with an insulating oil which electrically insulates the X-ray tube 210 and serves as a cooling medium. The insulating oil filling the container 220 is guided to a cooler through a pipe connected to the container 220 of the X-ray tube device 101, dissipates heat at the cooler, and returns to the container 220 through the pipe.

Most of heat generated at the X-ray focal point is dissipated to the envelope 213 due to radiation from a surface of the anode 212, and remaining heat flows toward the envelope 213 through the rotation body support 215 due to thermal conduction. The anode 212 is maintained at an average temperature of about 1000° C., and the rotation body support 215 is maintained at about several hundreds of ° C. due to heat flow like this, so that each portion of the X-ray tube 210 thermally expands. Thus, an X-ray focal point changes in the Z direction. The change amount measurement unit 300 is used to measure a change amount of the X-ray focal point.

Figure 3:
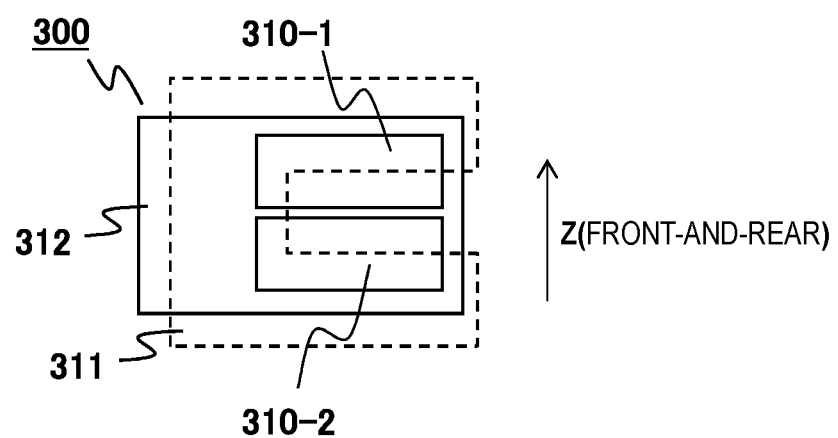
FIG. 3 is a diagram illustrating an example of a change amount measurement unit which measures a change amount of an X-ray focal point.

With reference to FIG. 3, a description will be made of a configuration of the change amount measurement unit 300. The change amount measurement unit 300 includes X-ray detection elements 310-1 and 310-2 detecting X-rays, and a slit 311. Each of the X-ray detection elements 310-1 and 310-2 is an element which outputs an electrical signal corresponding to a dose of incident X-rays, and are disposed to be arranged in the Z direction on a substrate 312. The slit 311 is made of metal whose X-ray shielding ratio is high, for example, tungsten, molybdenum, lead, or brass, has a recessed shape as indicated by a dashed line in FIG. 3, and is disposed apart from X-ray incidence surfaces of the X-ray detection elements 310-1 and 310-2. The center between the X-ray detection elements 310-1 and 310-2 and the center of the slit 311 are positioned with each other in the Z direction.

According to the change amount measurement unit 300 illustrated in FIG. 3, X-rays emitted from the X-ray tube device 101 are incident to the X-ray detection elements 310-1 and 310-2 via the slit 311. A dose of the X-rays incident to each of the X-ray detection elements 310-1 and 310-2 changes depending on a change in the X-ray focal point in the Z direction. In other words, if the X-ray focal point is moved in the positive Z direction, an output signal from the X-ray detection element 310-2 increases, and if the X-ray focal point is moved in the negative Z direction, an output signal from the X-ray detection element 310-1 increases. Thus, output signals from the respective X-ray detection elements 310-1 and 310-2 are detected, a difference value between both of the two signals is calculated, and thus a change amount of the X-ray focal point can be measured.

With reference to FIG. 4, a description will be made of various factors of causing a change in an X-ray focal point. In the X-ray tube 210 in a normal state, principal factors of causing a change in an X-ray focal point are thermal expansion of each portion of the X-ray tube 210 and centrifugal force applied to the X-ray tube 210 due to rotation of the rotation disk 102. Anomalies in the X-ray tube 210 as factors of causing a change in an X-ray focal point include an anomaly in the filament of the cathode 211 and an anomaly in the rotation body support 215. The anomaly in the filament may be, for example, disconnection or positional deviation, and, here, positional deviation of the filament causing a change in an X-ray focal point will be described. Hereinafter, a description will be made of a state in which an X-ray focal point changes due to each factor. In FIG. 4, a solid line indicates a state before a change occurs, and a dotted line indicates a state after the change occurs.

FIG. 4(a) illustrates a state in which an X-ray focal point changes due to thermal expansion. As described above, the anode 212 is heated as a result of collision of the electron beam 216 so that each portion of the X-ray tube 210, for example, the rotation body support 215 thermally expands, and thus the anode 212 is moved in the positive Z direction. As a result, an X-ray focal point changes in the positive Z direction. A change amount of the X-ray focal point is substantially proportional to a heat quantity accumulated in the anode 212. The heat quantity accumulated in the anode 212 can be substantially estimated on the basis of scanning conditions.

FIG. 4(b) illustrates a state in which an X-ray focal point changes due to centrifugal force. The centrifugal force caused by rotation of the rotation disk 102 is applied to the X-ray tube 210 in a direction orthogonal to the Z direction, and thus the anode 212 is moved in the direction orthogonal to the Z direction. As a result, an X-ray focal point changes in the negative Z direction. A change amount of the X-ray focal point is substantially proportional to the square of a rotation speed of the rotation disk 102.

FIG. 4(c) illustrates a state in which an X-ray focal point changes due to an anomaly in the filament of the cathode 211. In a case where positional deviation occurs in the filament, a position where the electron beam 216 collides with the anode 212, that is, a position of an X-ray focal point is deviated relative to a regular position. A change amount of the X-ray focal point increases according to a positional deviation amount of the filament. The positional deviation of the filament frequently suddenly occurs.

FIG. 4(d) illustrates a state in which an X-ray focal point changes due to an anomaly in the rotation body support 215. In a case where an anomaly occurs in the rotation body support 215, the rotation axis of the rotation body support 215 is deviated, and thus an X-ray focal point vibrates in synchronization with the number of rotations of the anode 212. An vibration amount of the X-ray focal point increases according to a deviation amount of the rotation axis. The deviation of the rotation axis of the rotation body support 215 tends to increase as use time increases.

A change amount of an X-ray focal point due to an anomaly in the X-ray tube 210 is added to a change amount in the X-ray tube 210 in a normal state. Whereas a change amount in a normal state can be substantially estimated on the basis of scanning conditions, a change amount when an anomaly occurs increases according to the extent of the anomaly. In other words, a change amount of an X-ray focal point in a normal state, which can be estimated on the basis of scanning conditions is compared with a change amount measured during scanning, and thus it is possible to determine whether or not an anomaly occurs in the X-ray tube 210.

An allowance range to which a measurement error of the change amount measurement unit 300, time delay of thermal expansion, or a variation in a rotation speed is added is preferably set in a change amount of an X-ray focal point in the X-ray tube 210 in a normal state. In other words, it is preferable to set a normal change range which is a change range obtained by adding the allowable range to a change amount in a normal state. Also regarding vibration of an X-ray focal point caused by deviation of the rotation axis of the rotation body support 215, a normal vibration range is preferably set as an allowable vibration range.

With reference to FIG. 5, a description will be made of the normal change range of a change amount of an X-ray focal point and the normal vibration range of a vibration amount.

The normal change range is set according to factors of causing a change in an X-ray focal point, that is, thermal expansion and centrifugal force. Hereinafter, each thereof will be described.

With reference to FIG. 5 (a), the normal change range related to thermal expansion will be described. As described above, a change amount of an X-ray focal point due to thermal expansion is substantially proportional to a heat quantity accumulated in the anode 212. Therefore, in a two-dimensional space in which a transverse axis expresses an accumulated heat quantity, and a longitudinal axis expresses a change amount, the normal change range determined by adding an allowable range to a change amount of an X-ray focal point estimated on the basis of an accumulated heat quantity is set as illustrated in FIG. 5 (a). Instead of the change amount estimated on the basis of an accumulated heat quantity, a change amount measured while changing an accumulated heat quantity by using the X-ray tube 210 which is confirmed as being in a normal state may be used. In this case, conditions other than the accumulated heat quantity are preferably set to be the same.

With reference to FIG. 5(b), the normal change range related to centrifugal force will be described. As described above, a change amount of an X-ray focal point due to centrifugal force is substantially proportional to the square of a rotation speed of the rotation disk 102. Therefore, in a two-dimensional space in which a transverse axis expresses a rotation speed, and a longitudinal axis expresses a change amount, the normal change range determined by adding an allowable range to a change amount of an X-ray focal point estimated on the basis of a rotation speed is set as illustrated in FIG. 5(b). Instead of the change amount estimated on the basis of a rotation speed, a change amount measured while changing a rotation speed by using the X-ray tube 210 which is confirmed as being in a normal state and the rotation disk 102 may be used.

In this case, conditions other than the rotation speed are preferably set to be the same. In a case where an X-ray diagnostic imaging apparatus is not provided with the rotation disk 102, for example, in an X-ray fluoroscopic imaging apparatus, the normal change range regarding centrifugal force may not be handled.

In a case where the normal change range set in the above-described way is compared with a change amount measured during scanning, and the measured change amount does not fall within the normal change range, it may be determined that there is an anomaly in the X-ray tube 210. The outside of the normal change range is referred to as an abnormal change range.

With reference to FIG. 5(c), a description will be made of the normal vibration range related to deviation of the rotation axis of the rotation body support 215. A vibration amount of an X-ray focal point increases according to the extent of deviation of the rotation axis of the rotation body support 215. In a case where an anomaly occurs in the rotation body support 215, an X-ray focal point changes and vibrates in synchronization with the number of rotations of the anode 212 between the normal change range and the abnormal change range. The deviation of the rotation axis tends to increase according to use time of the X-ray tube 210. Therefore, in a two-dimensional space in which a transverse axis expresses cumulative use time as a result of cumulating use time, and a longitudinal axis expresses a vibration amount, a vibration amount which is allowable in an X-ray diagnostic imaging apparatus is set as the normal vibration range as illustrated in FIG. 5(c).

Instead of the vibration amount which is allowable in an X-ray diagnostic imaging apparatus, a vibration amount may be measured by using the X-ray tube 210 which is confirmed as being in a normal state, and the normal vibration range may be set on the basis of the measured vibration amount. For example, the maximum value of the measured vibration amount may be set as the normal vibration range.

In a case where the normal vibration range set in the above-described way is compared with a vibration amount measured while an X-ray diagnostic imaging apparatus is used, and the measured vibration amount falls within an abnormal vibration range other than the normal vibration range, it may be determined that there is an anomaly in the rotation body support 215 of the X-ray tube 210. Even if a vibration amount falls within the normal vibration range, in a case where a vibration amount starts to increase, the service life of the X-ray tube 210 may be estimated by using a measured vibration amount. In other words, the measured vibration amount is approximated to a curve when being regarded as a function of cumulative use time, cumulative use time in which the obtained curve reaches the abnormal vibration range is calculated, and thus the service life of the rotation body support 215 of the X-ray tube 210 can be estimated.

Figure 6:
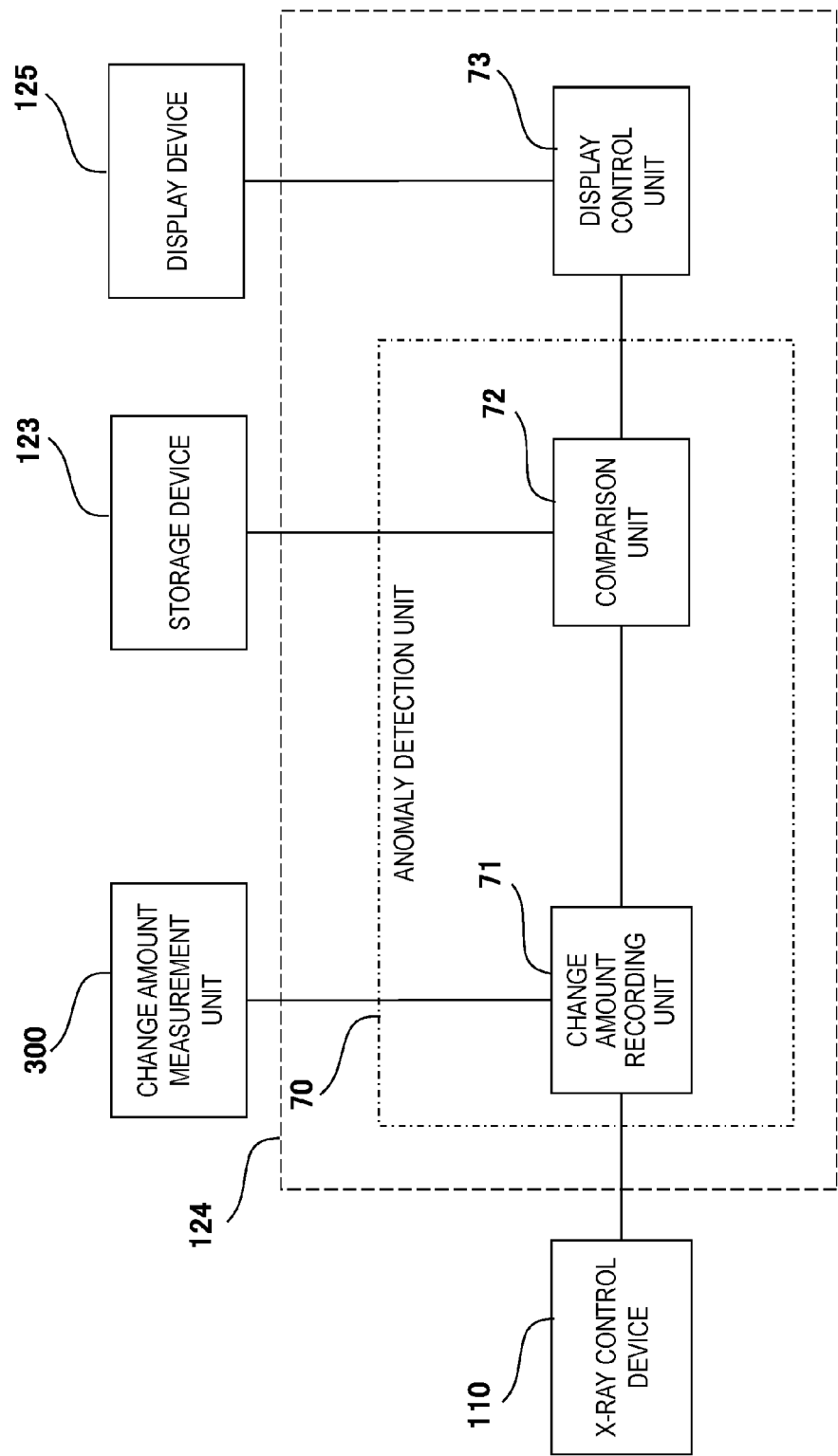
FIG. 6 is a block diagram illustrating principal constituent elements according to the first embodiment.

With reference to FIG. 6, principal constituent elements of the present embodiment will be described. The principal constituent elements may be configured by using dedicated hardware, and may be configured by using software operating on the system control device 124. Here, a description will be made of a case where the constituent elements are configured by using software.

In the present embodiment, an anomaly detection unit 70 and a display control unit 73 are provided. The storage device 123 stores the normal change ranges as illustrated in FIG. 5. Here, the respective constituent units will be described.

The anomaly detection unit 70 detects an anomaly in the X-ray tube 210 on the basis of whether or not a change amount of an X-ray focal point measured during scanning falls within the normal change range which is a predetermined change range. The anomaly detection unit 70 includes a change amount recording unit 71 and a comparison unit 72 each of which will now be described.

The change amount recording unit 71 records a change amount of an X-ray focal point measured during scanning in correlation with scanning conditions. In other words, the change amount recording unit 71 acquires a change amount of an X-ray focal point measured during scanning from the change amount measurement unit 300, acquires scanning conditions during scanning from the X-ray control device 110, and records the change amount and the scanning conditions in correlation with each other. Specifically, for example, in order that a measured change amount can be plotted in the two-dimensional space in FIG. 5(a), X-ray irradiation conditions are extracted from scanning conditions when the change amount is measured, an accumulated heat quantity is calculated on the basis of the extracted X-ray irradiation conditions, and the calculated accumulated heat quantity is correlated with the measured change amount.

The comparison unit 72 compares the change amount correlated with the scanning conditions with the normal change range so as to determine whether or not there is an anomaly in the X-ray tube 210. In other words, the comparison unit 72 acquires a change amount correlated with the scanning conditions from the change amount recording unit 71, acquires the normal change range from the storage device 123, and compares the change amount with the normal change range. Specifically, normality is determined if the change amount plotted in the two-dimensional space in FIG. 5(a) by the change amount recording unit 71 falls within the normal change range, and an anomaly is determined if the change amount falls within the abnormal change range.

The display control unit 73 controls display on the display device 125 depending on whether or not there is an anomaly in the X-ray tube 210. In other words, the display control unit 73 receives a determination result such as normality or an anomaly from the comparison unit 72, and controls the content displayed on the display device 125 depending on the determination result. Specifically, the determination result from the comparison unit 72 may be displayed without being changed, and, only in a case where there is an anomaly in the X-ray tube 210, the occurrence of the anomaly may be displayed.

Figure 7:
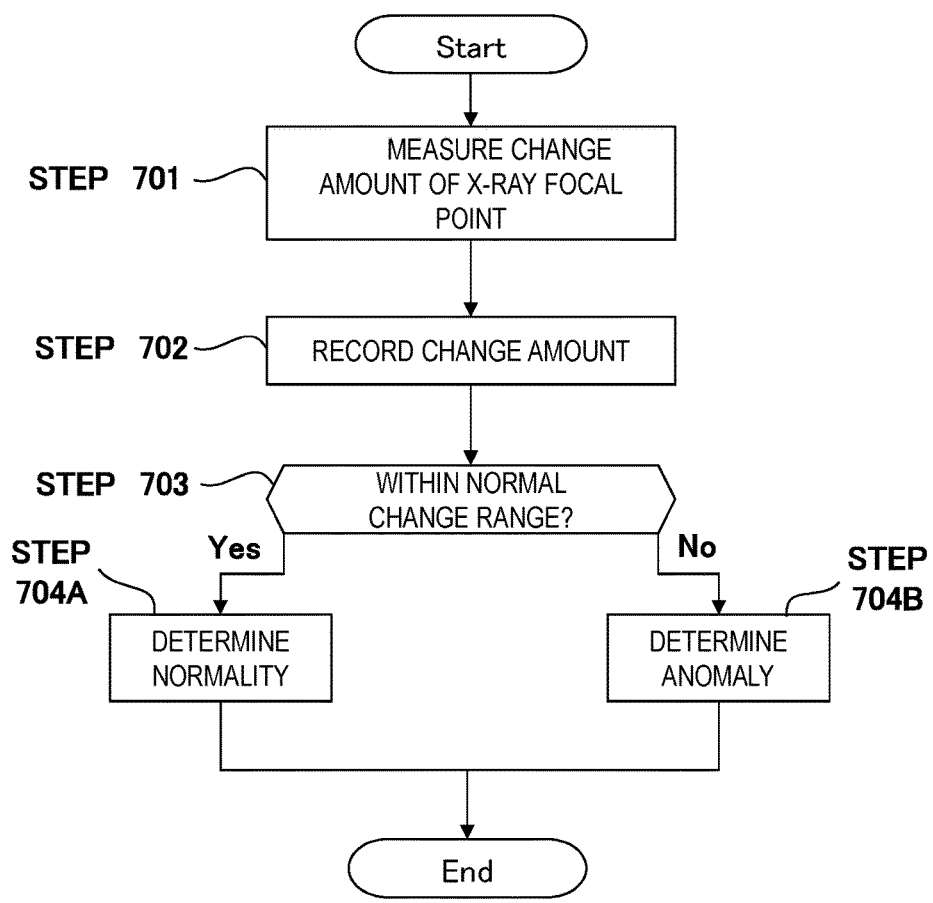
FIG. 7 is a diagram illustrating a flow of a process according to the first embodiment.

With reference to FIG. 7, a description will be made of an example of a flow of a process performed by the X-ray diagnostic imaging apparatus including the constituent units.

(Step 701)

The change amount measurement unit 300 measures a change amount of an X-ray focal point during scanning of an X-ray image.

(Step 702)

The change amount recording unit 71 records the change amount measured in step 701 in correlation with scanning conditions during scanning.

(Step 703)

The comparison unit 72 compares the change amount recorded in step 701 with the normal change range. If the change amount falls within the normal change range, the flow proceeds to step 704A, and if otherwise, the flow proceeds to step 704B.

(Step 704A)

The display control unit 73 displays that the X-ray tube 210 is normal on the display device 125. In a case where an operator is troubled with display indicating that the X-ray tube 210 is normal, the display device 125 may not perform normality display.

(Step 704B)

The display control unit 73 displays that an anomaly occurs in the X-ray tub 210 on the display device 125.

The X-ray diagnostic imaging apparatus executes the flow of the above-described process, and can thus detect an anomaly in the X-ray tube 210.

[Second Embodiment]

Next, a second embodiment will be described. In the first embodiment, a description has been made of a case of detecting an anomaly in the X-ray tube 210. In the present embodiment, a location where an anomaly occurs in the X-ray tube 210 is specified. Hereinafter, differences between the first embodiment and the second embodiment will be described in detail, and description of the same configurations as those in the first embodiment will be omitted.

Figure 8:
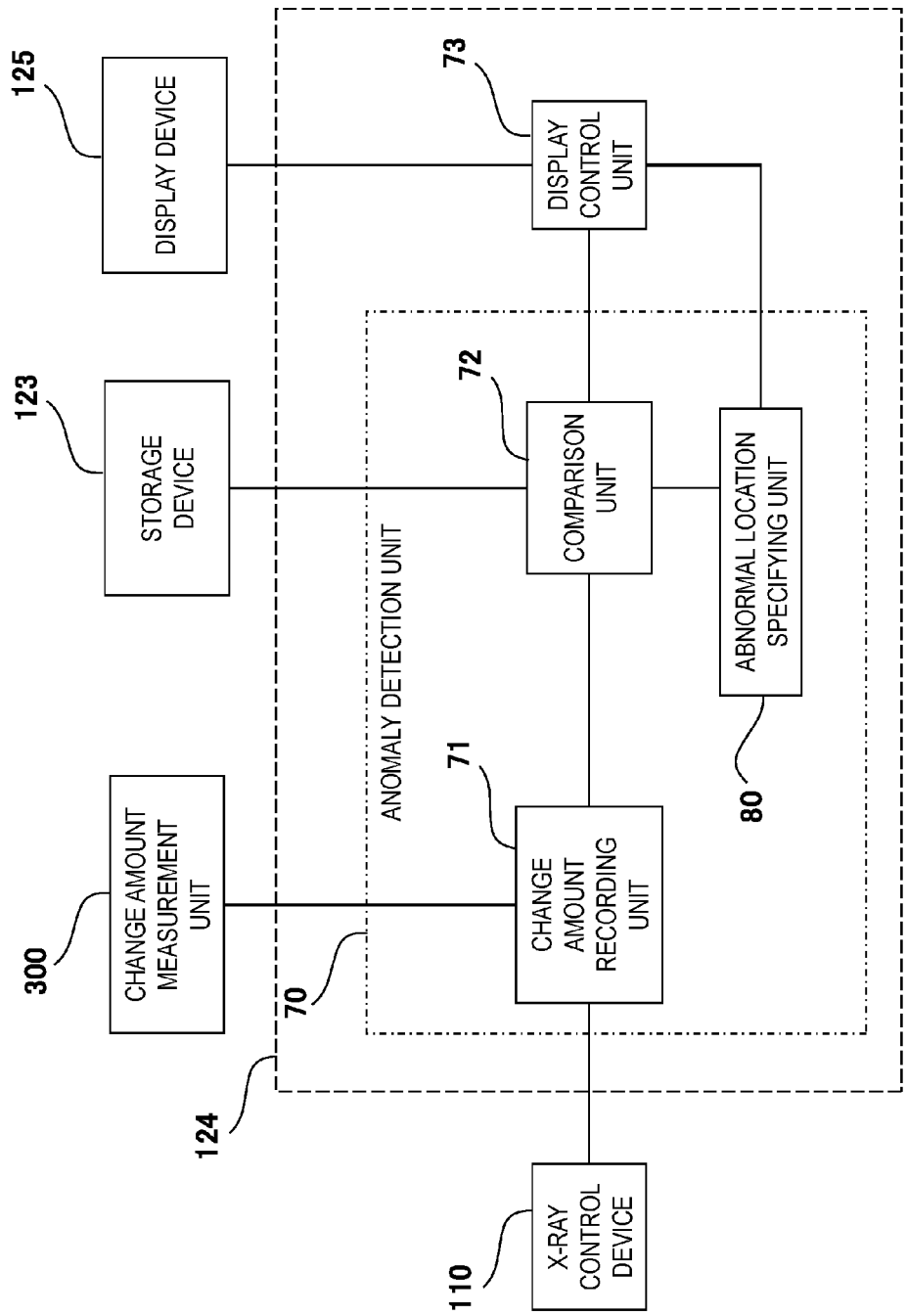
FIG. 8 is a block diagram illustrating principal constituent elements according to a second embodiment.

With reference to FIG. 8, principal constituent elements of the present embodiment will be described. In the present embodiment, the anomaly detection unit 70 further includes an abnormal location specifying unit 80 in the configuration of the first embodiment. The abnormal location specifying unit 80 specifies an anomaly location on the basis of a comparison result between a measured change amount of an X-ray focal point and the normal change range.

In other words, when the comparison unit 72 determines that there is an anomaly, the abnormal location specifying unit 80 receives a comparison result between a measured change amount and the normal change range from the comparison unit 72. In a case where a period in which the change amount falls within the abnormal change range is more than a threshold value, it is specified that there is an anomaly in the filament of the cathode 211. In a case where the change amount vibrates between the normal change range and the abnormal change range, it is specified that there is an anomaly in the rotation body support 215. An X-ray focal point vibrates in synchronization with rotation of the anode 212. For example, the number of rotations of the anode 212 is sixty per second, and thus one second is set as the threshold value. The specified abnormal location is transmitted to the display control unit 73, and the display control unit 73 displays the specified abnormal location on the display device 125.

Figure 9:
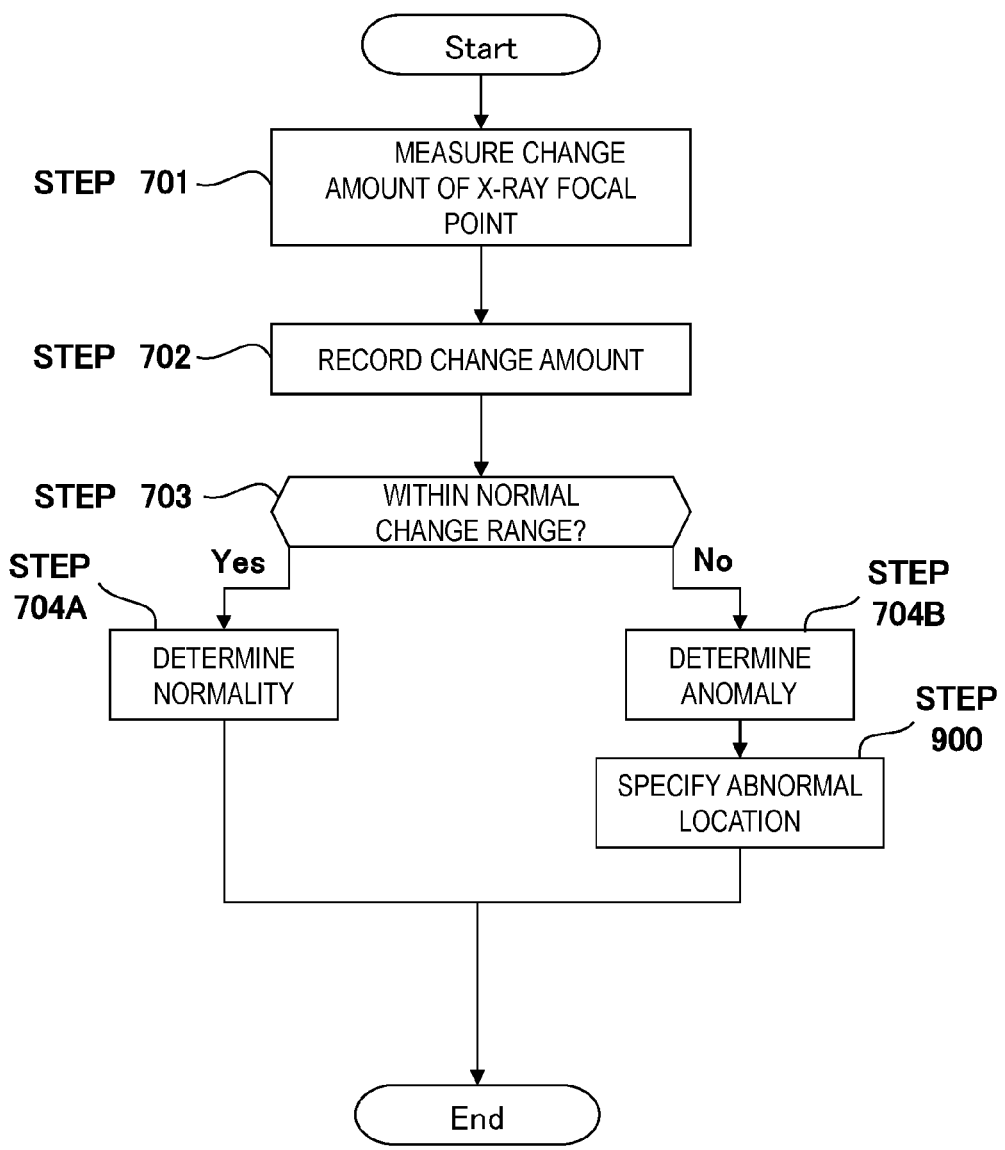
FIG. 9 is a diagram illustrating a flow of a process according to the second embodiment.

With reference to FIG. 9, a description will be made of an example of a flow of a process performed by the X-ray diagnostic imaging apparatus including the constituent units.

(Step 701 to Step 704A)

Processes in these steps are the same as those in the first embodiment.

(Step 704B)

In the same manner as in the first embodiment, the display control unit 73 displays that an anomaly occurs in the X-ray tube 210 on the display device 125, but then proceeds to step 900.

(Step 900)

The abnormal location specifying unit 80 specifies an abnormal location in the X-ray tube 210 on the basis of a period in which the measured change amount falls within the abnormal change range. In other words, in a case where the period in which the change amount falls within the abnormal change range is more than a set threshold value, the filament of the cathode 211 is specified as an abnormal location. In a case where the change amount vibrates between the normal change range and the abnormal change range, the rotation body support 215 is specified as an abnormal location. The specified abnormal location is displayed on the display device 125 by the display control unit 73.

The X-ray diagnostic imaging apparatus performs the flow of the process, and can thus detect an anomaly in the X-ray tube 210 and can also specify an abnormal location.

[Third Embodiment]

Next, a third embodiment will be described. In the first embodiment, a description has been made of a case of detecting an anomaly in the X-ray tube 210. In the present embodiment, the service life of the X-ray tube 210 is estimated. Hereinafter, differences between the first embodiment and the third embodiment will be described in detail, and description of the same configurations as those in the first embodiment will be omitted.

Figure 10:
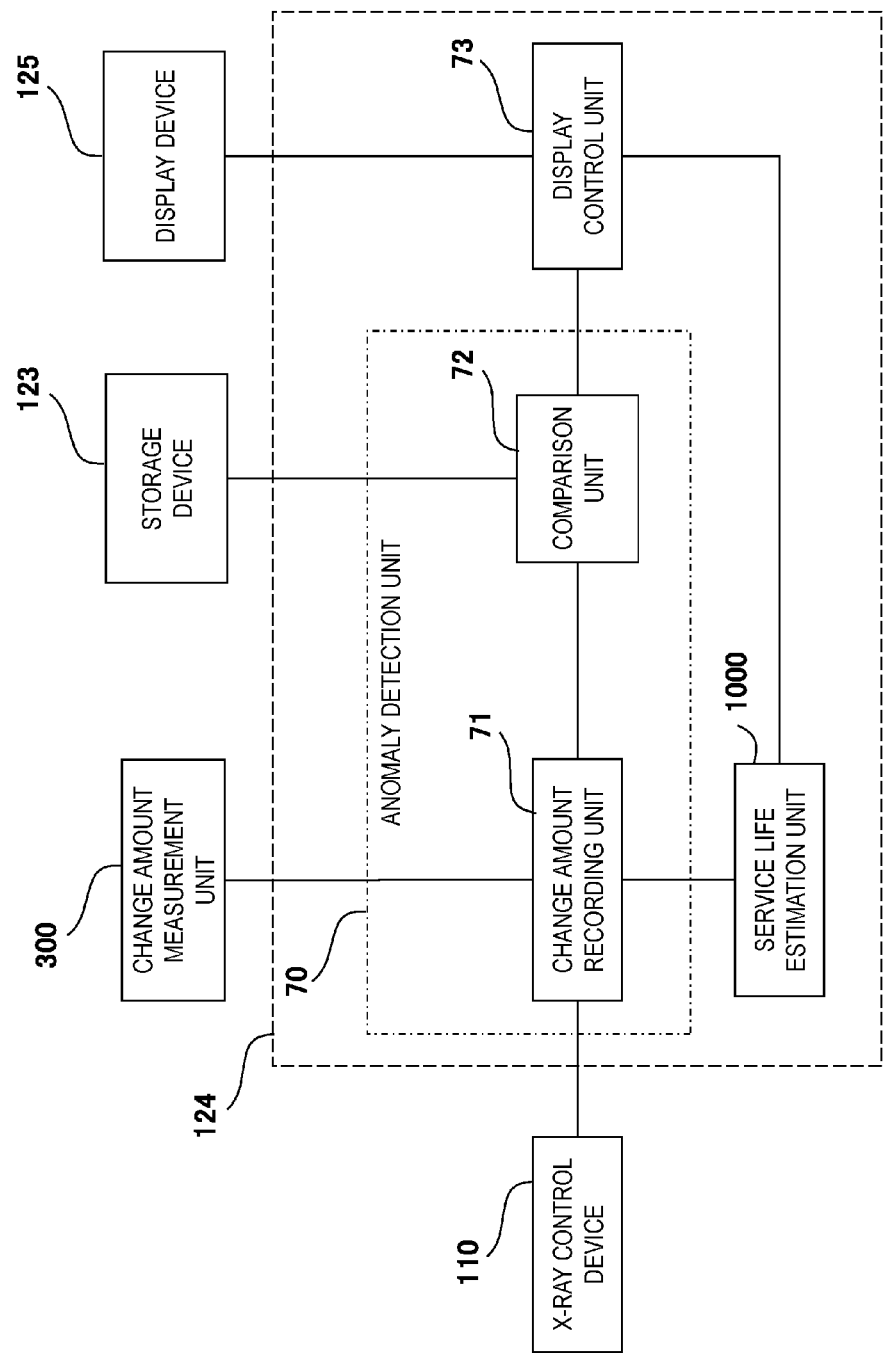
FIG. 10 is a block diagram illustrating principal constituent elements according to a third embodiment.

With reference to FIG. 10, principal constituent elements of the present embodiment will be described. In the present embodiment, a service life estimation unit 1000 is further provided in the configuration of the first embodiment. The service life estimation unit 1000 estimates the service life of the rotation body support 215 of the X-ray tube 210 on the basis of a measured vibration amount of an X-ray focal point. In other words, the service life estimation unit 1000 regards a measured vibration amount as a function of cumulative use time of the X-ray diagnostic imaging apparatus so as to approximate the vibration amount to a curve, calculates cumulative use time in which the obtained curve reaches the abnormal vibration range, and thus estimates the service life of the rotation body support 215 of the X-ray tube 210. The estimated service life is transmitted to the display control unit 73, and the display control unit 73 displays the estimated service life on the display device 125.

Figure 11:
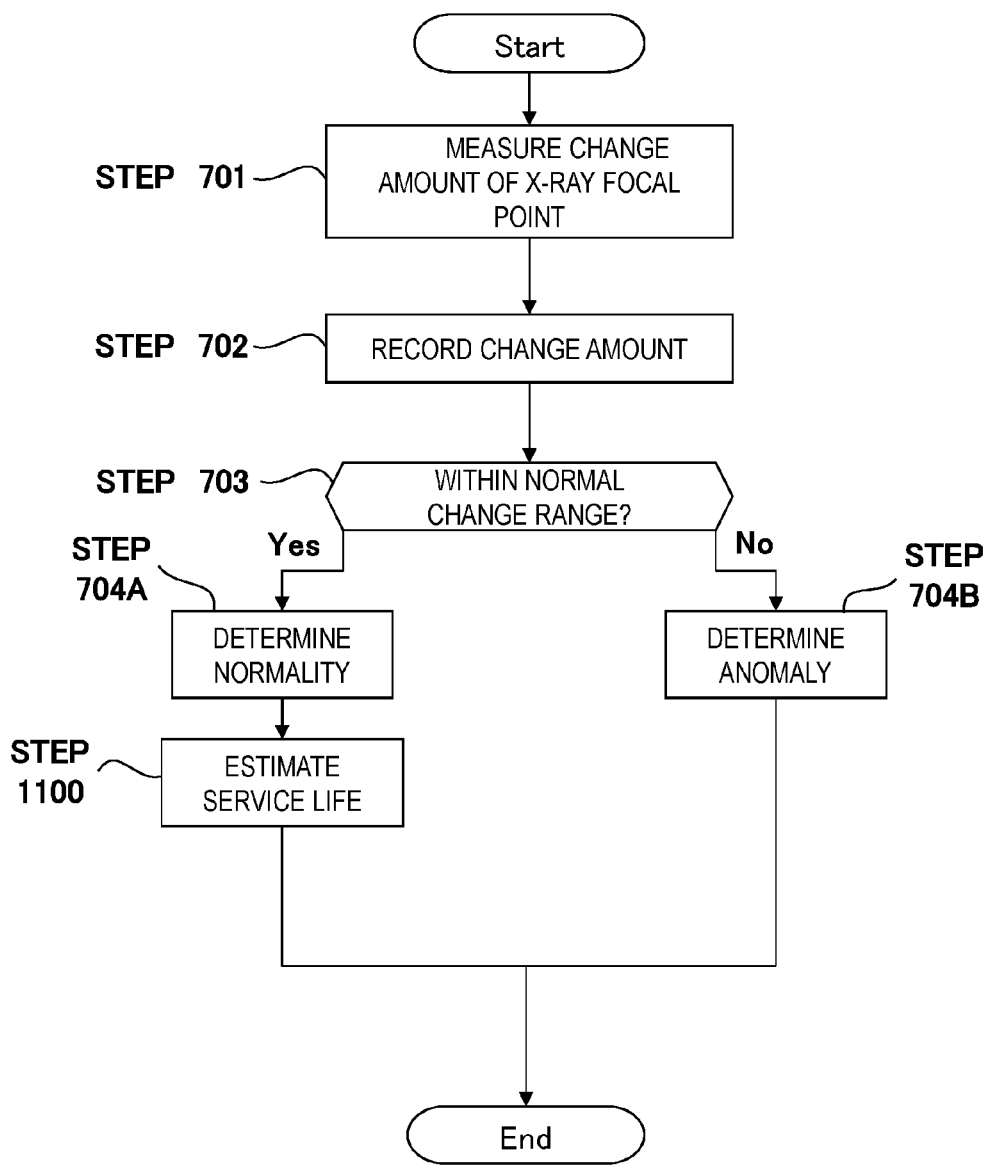
FIG. 11 is a diagram illustrating a flow of a process according to the third embodiment.

With reference to FIG. 11, a description will be made of an example of a flow of a process performed by the X-ray diagnostic imaging apparatus including the constituent units.

(Step 701 to Step 703, and Step 704B)

Processes in these steps are the same as those in the first embodiment.

(Step 704A)

In the same manner as in the first embodiment, the display control unit 73 displays that the X-ray tube 210 is normal on the display device 125 or does not perform any operation, but then proceeds to step 1100.

(Step 1100)

The service life estimation unit 1000 estimates the service life of the rotation body support 215 of the X-ray tube 210 on the basis of the measured vibration amount of an X-ray focal point. The estimated service life is displayed on the display device 125 by the display control unit 73. Regarding a service life display form, residual use time may be displayed, and the time to reach an abnormal vibration range measured on the basis of a use frequency and residual use time of the X-ray diagnostic imaging apparatus may be displayed.

The X-ray diagnostic imaging apparatus performs the flow of the process, and can thus detect an anomaly in the X-ray tube 210 and can also predict the time at which an anomaly will occur in the X-ray tube 210.

[Fourth Embodiment]

Next, a fourth embodiment will be described. In the first embodiment, a description has been made of a case of detecting an anomaly in the X-ray tube 210 on the basis of a relationship between an accumulated heat quantity and a change amount. In the present embodiment, an anomaly in the X-ray tube 210 is further detected by taking into consideration a relationship between a rotation speed of the rotation disk 102 and a change amount. Hereinafter, differences between the first embodiment and the fourth embodiment will be described in detail, and description of the same configurations as those in the first embodiment will be omitted.

Figure 12:
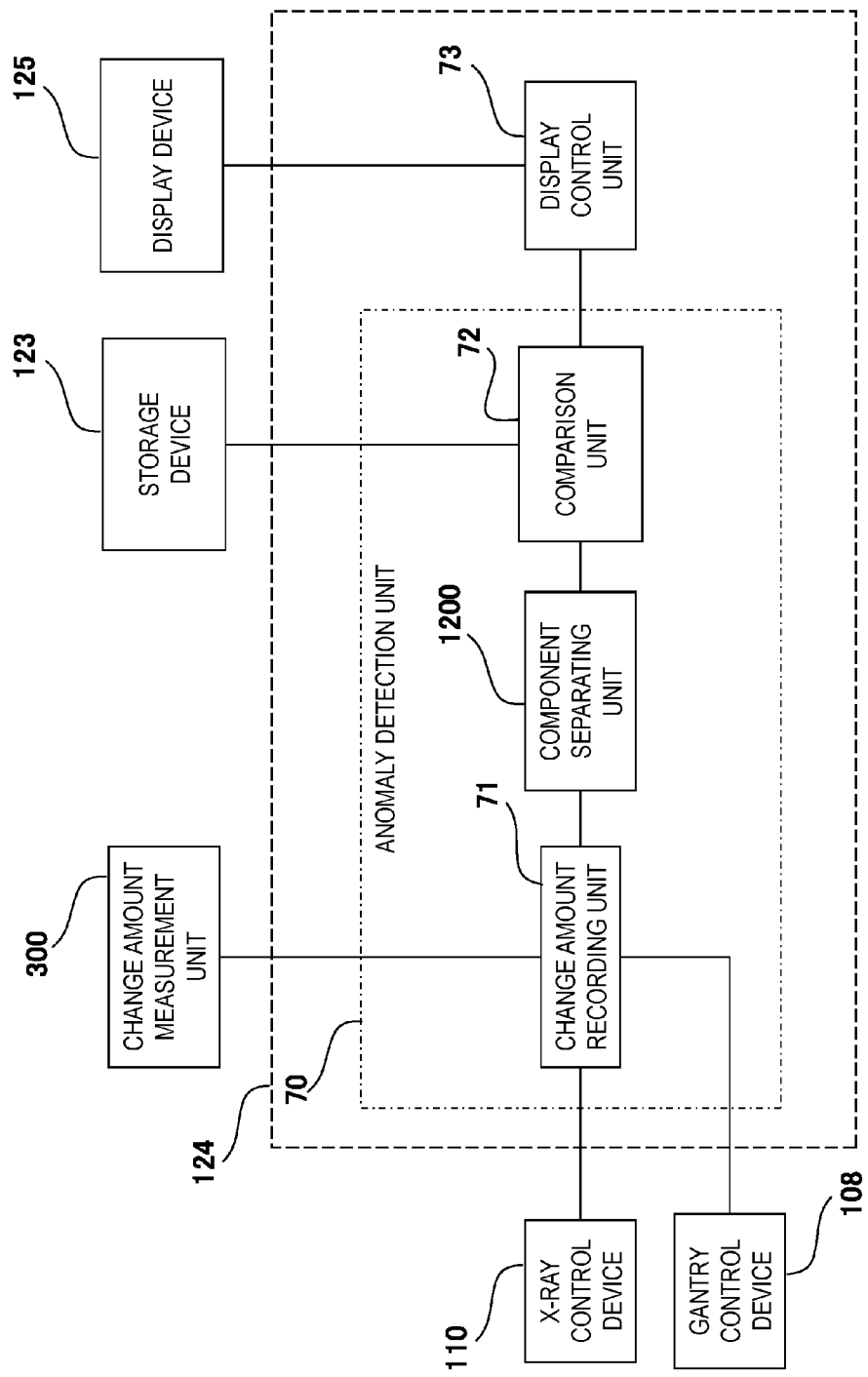
FIG. 12 is a block diagram illustrating principal constituent elements according to a fourth embodiment.

With reference to FIG. 12, principal constituent elements of the present embodiment will be described. In the present embodiment, a component separating unit 1200 is further provided in the configuration of the first embodiment. The change amount recording unit 71 and the comparison unit 72 perform a process related to a rotation speed of the rotation disk 102 along with a process related to an accumulated heat quantity. Hereinafter, the change amount recording unit 71, the component separating unit 1200, the comparison unit 72 will be described.

The change amount recording unit 71 records a change amount of an X-ray focal point measured during scanning in correlation with scanning conditions. In other words, the change amount recording unit 71 acquires a change amount of an X-ray focal point measured during scanning from the change amount measurement unit 300, acquires scanning conditions during scanning from the X-ray control device 110 and the gantry control device 108, and records the change amount and the scanning conditions in correlation with each other.

Specifically, for example, in order that a measured change amount can be plotted in the two-dimensional space in FIG. 5(a), X-ray irradiation conditions are extracted from scanning conditions when the change amount is measured, an accumulated heat quantity is calculated on the basis of the extracted X-ray irradiation conditions, and the calculated accumulated heat quantity is correlated with the measured change amount.

In order that a measured change amount can be plotted in the two-dimensional space in FIG. 5(b), a rotation speed of the rotation disk 102 is extracted from scanning conditions when the change amount is measured, and the extracted rotation speed is correlated with the measured change amount.

The component separating unit 1200 separates the measured change amount of an X-ray focal point into a thermal expansion component related to thermal expansion and a centrifugal force component related to centrifugal force. In other words, the component separating unit 1200 acquires change amounts correlated with the scanning conditions from the change amount recording unit 71, and sorts change amounts correlated with an accumulated heat quantity calculated on the basis of the scanning conditions or the extracted rotation speed, so as to separate the change amounts into a thermal expansion component and a centrifugal force component.

Specifically, in the two-dimensional space having the axes of a change amount and an accumulated heat quantity as illustrated in FIG. 5(a), a change amount measured at each rotation speed is plotted. In the two-dimensional space having the axes of a change amount and a rotation speed as illustrated in FIG. 5(b), a change amount measured at each accumulated heat quantity is plotted.

The comparison unit 72 compares the change amounts which are separated into the thermal expansion component and the centrifugal force component with the normal change range, so as to determine the presence or absence of an anomaly in the X-ray tube 210. In other words, the comparison unit 72 acquires the thermal expansion component and the centrifugal force component of the change amounts from the component separating unit 1200, also acquires the normal change range from the storage device 123, and compares each of the thermal expansion component and the centrifugal force component with the normal change range.

Specifically, if the thermal expansion component of the change amount plotted in the two-dimensional space in FIG. 5(a) and the centrifugal force component of the change amount plotted in the two-dimensional space in FIG. 5(b) by the component separating unit 1200 fall within the normal change range, normality is determined, and if the two components fall within the abnormal change range, an anomaly is determined. Regarding the normal change range stored in the storage device 123, a differing normal change range is set for each rotation speed in an space formed of a change amount and an accumulated heat quantity, and a differing normal change range is set for each accumulated heat quantity in a space formed of a change amount and a rotation speed.

Figure 13:
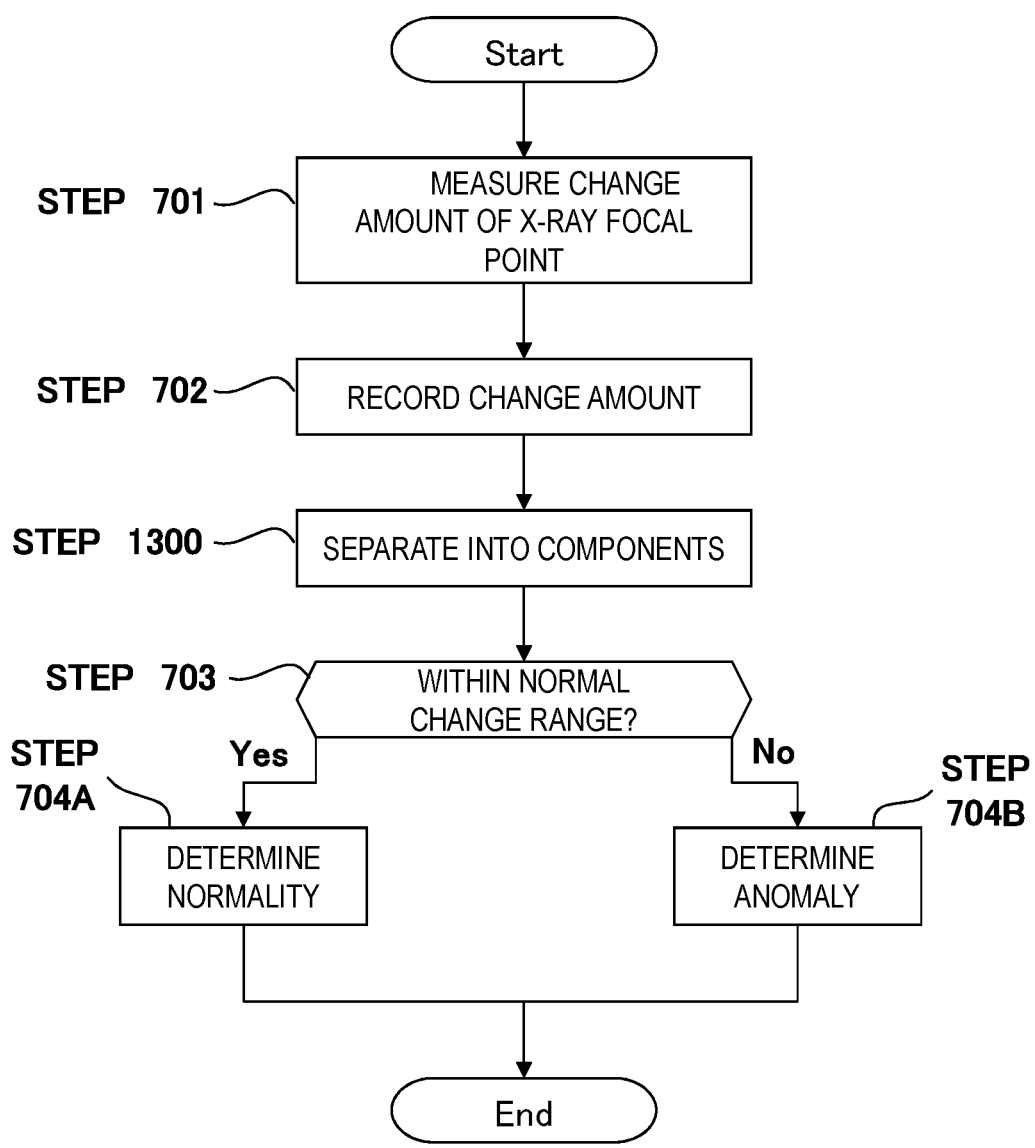
FIG. 13 is a diagram illustrating a flow of a process according to the fourth embodiment.

With reference to FIG. 13, a description will be made of an example of a flow of a process performed by the X-ray diagnostic imaging apparatus including the constituent units.

(Step 701)

A process in this step is the same as that in the first embodiment.

(Step 702)

In the same manner as in the first embodiment, the change amount recording unit 71 records the change amount measured in step 701 in correlation with scanning conditions during scanning. Specifically, an accumulated heat quantity and a rotation speed, and a measured change amount are recorded in correlation with each other.

(Step 1300)

The component separating unit 1200 separates the measured change amount of an X-ray focal point into a thermal expansion component and a centrifugal force component.

(Step 703)

The comparison unit 72 compares each of the thermal expansion component and the centrifugal force component as a result of the separation in step 1300 with the normal change range. If the change amount falls within the normal change range, the flow proceeds to step 704A, and if otherwise, the flow proceeds to step 704B.

(Step 704A and Step 704B)

Processes in these steps are the same as those in the first embodiment.

The X-ray diagnostic imaging apparatus executes the flow of the above-described process, and can thus detect an anomaly in the X-ray tube 210. Since a change amount is separated into a thermal expansion component and a centrifugal force component, and then the presence or absence of an anomaly is determined, detection accuracy can be further improved.

[Fifth Embodiment]

Next, a fifth embodiment will be described. In the first to fourth embodiments, a description has been made of a case where anomaly detection of the X-ray tube 210 based on a change amount of an X-ray focal point during scanning is performed for each X-ray diagnostic imaging apparatus. In the present embodiment, a description will be made of a case where a change amount of an X-ray focal point measured for each X-ray diagnostic imaging apparatus is collected by the monitoring server, and is collectively managed.

Figure 14:
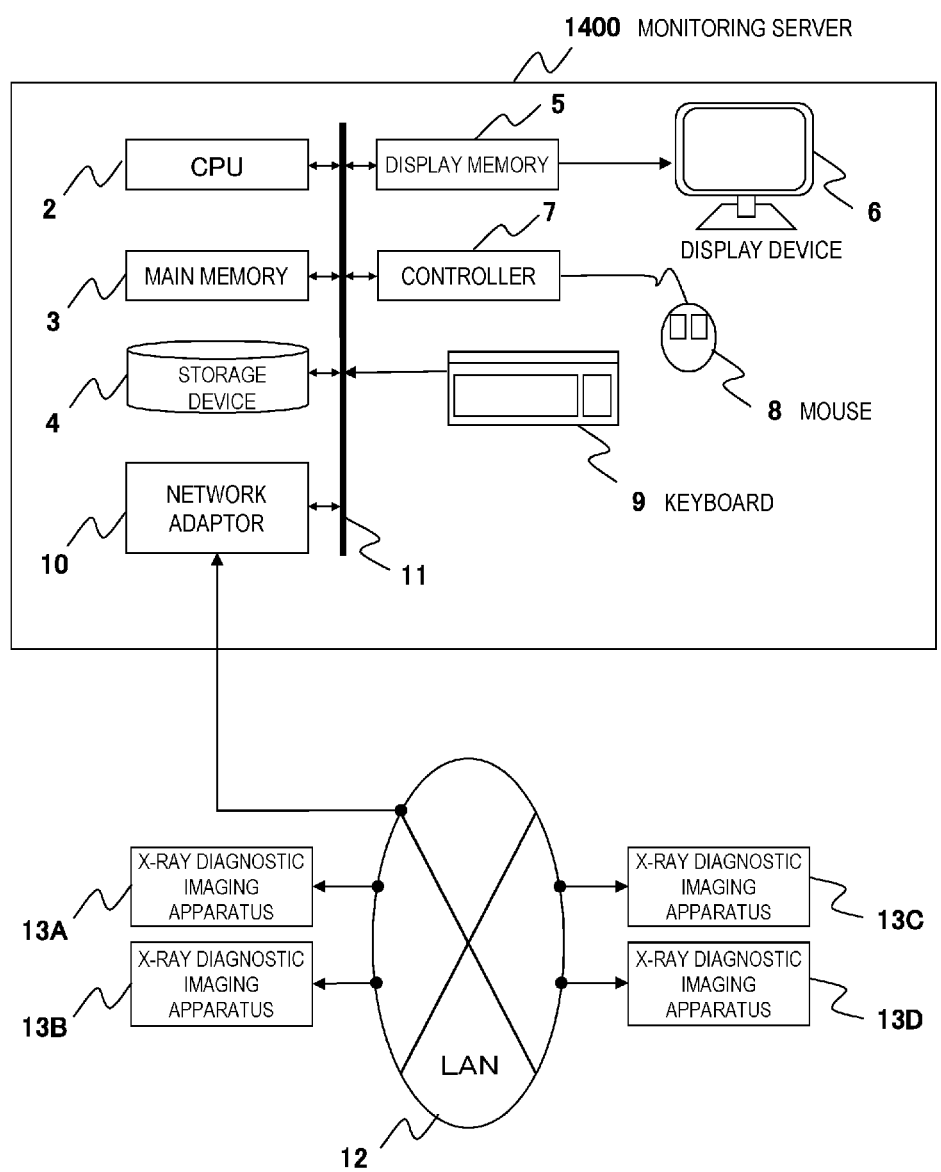
FIG. 14 is a diagram illustrating a configuration of a system which monitors an X-ray diagnostic imaging apparatus according to a fifth embodiment.

With reference to FIG. 14, a description will be made of a configuration of a system monitoring the X-ray diagnostic imaging apparatus of the present embodiment. The present system includes a plurality of X-ray diagnostic imaging apparatuses 13A to 13D, a monitoring server 1400, and a network 12 connecting the apparatuses to the server.

Each of the plurality of X-ray diagnostic imaging apparatuses 13A to 13D is the X-ray diagnostic imaging apparatus described in the first to fourth embodiments, and is provided in a remote hospital or the like.

The monitoring server 1400 is configured to include a central processing unit (CPU) 2, a main memory 3, a storage device 4, a display memory 5, a display device 6, a controller 7 connected to a mouse 8, a keyboard 9, and a network adaptor 10 which can be connected to each other via a system bus 11 so as to transmit and receive signals. The monitoring server 1400 is connected to the X-ray diagnostic imaging apparatuses 13A to 13D via the network 12. The network 12 may employ a wired communication type or a wireless communication type as long as signals can be electrically or optically transmitted and received via the network.

The CPU 2 is a device controlling an operation of each constituent element of the monitoring server 1400. The CPU 2 loads a program stored in the storage device 4 or data required to execute the program to the main memory 3, and executes the program. The storage device 4 is a device storing a program executed by the CPU 2 or data required to execute the program, and is, specifically, a hard disk or the like.

The main memory 3 stores a program executed by the CPU 2 or a result in the middle of a calculation process. The display memory 5 temporarily stores display data to be displayed on the display device 6 such as a liquid crystal display or a cathode ray tube (CRT). The mouse 8 or the keyboard 9 is an operation device for an operator to give an operation instruction to the monitoring server 1400. The mouse 8 may be other pointing devices such as a track pad or a track ball.

The controller 7 detects a state of the mouse 8 so as to acquire a position of a mouse pointer on the display device 6, and outputs acquired position information or the like to the CPU 2. The network adaptor 10 connects the monitoring server 1400 to the network 12 such as a LAN, a telephone line, or the Internet.

In each of the X-ray diagnostic imaging apparatuses 13A to 13D, data regarding a change amount of an X-ray focal point recorded in correlation with scanning conditions or a determination result based on the change amount, a specified abnormal location, and the estimated service life is transmitted to the monitoring server 1400 via the network 12. The transmitted data is stored in the storage device 4 so as to be collectively managed.

Some of the transmitted pieces of data are displayed on the display device 6, and a state of the X-ray diagnostic imaging apparatuses 13A to 13D is presented to an operator. The operator checks a state of each of the X-ray diagnostic imaging apparatuses 13A to 13D, for example, the service life of the X-ray tube 210 so as to be able to plan the replacement time of the X-ray tube 210.

The monitoring server 1400 may detect an anomaly in the X-ray tube 210, specify an abnormal location in the X-ray tube 210, or estimate the service life of the X-ray tube 210 on the basis of the data regarding a change amount of an X-ray focal point transmitted from each of the X-ray diagnostic imaging apparatuses 13A to 13D. The monitoring server may plan and display the replacement time of the X-ray tube 210 on the basis of the service life of each X-ray tube 210.

The monitoring server 1400 may present a location to be inspected in each of the X-ray diagnostic imaging apparatuses 13A to 13D on the basis of the history of abnormal locations occurring in the X-ray diagnostic imaging apparatuses 13A to 13D.

For example, in a case where an anomaly frequently occurs in the filament of the cathode 211 in a certain X-ray diagnostic imaging apparatus, there is a probability that there may be an anomaly in a circuit supplying power to the filament so that excessive power is suddenly supplied to the filament, and this may cause positional deviation of the filament. Therefore, in a case where an anomaly frequently occurs in the filament, the monitoring server 1400 may present and display the circuit supplying power to the filament as a location to be inspected.

In a case where an anomaly frequently occurs in the rotation body support 215 in a certain X-ray diagnostic imaging apparatus, there is a probability that dynamic balance of the rotation disk 102 may be deviated. Therefore, in a case where an anomaly frequently occurs in the rotation body support 215, the monitoring server 1400 may present and display inspection of the dynamic balance of the rotation disk 102.

A medical image display device of the present invention is not limited to the above-described embodiments, and may be embedded by modifying constituent elements within the scope without departing from the spirit of the invention. A plurality of constituent elements disclosed in the embodiments may be combined with each other as appropriate. For example, the component separating unit 1200 described in the fourth embodiment may be combined with the configuration of the second embodiment or the third embodiment. Some constituent elements may be deleted from all of the constituent elements described in the embodiments. For example, in the first to fourth embodiments, the display control unit 73 may not display an anomaly detected by the anomaly detection unit 70 on the display device 125 but may notify an operator of the anomaly in voices or the like.

REFERENCE SIGNS LIST

1 X-RAY CT APPARATUS, 100 SCAN GANTRY UNIT, 101 X-RAY TUBE DEVICE, 102 ROTATION DISK, 103 COLLIMATOR, 104 OPENING, 105 BED, 106 X-RAY DETECTOR, 107 DATA COLLECTING DEVICE, 108 GANTRY CONTROL DEVICE, 109 BED CONTROL DEVICE, 110 X-RAY CONTROL DEVICE, 120 OPERATION CONSOLE, 121 INPUT DEVICE, 122 IMAGE CALCULATION DEVICE, 123 STORAGE DEVICE, 124 SYSTEM CONTROL DEVICE, 125 DISPLAY DEVICE, 210 X-RAY TUBE, 211 CATHODE, 212 ANODE, 213 ENVELOPE, 214 EXCITATION COIL, 215 ROTATION BODY SUPPORT, 216 ELECTRON BEAM, 217 X-RAY, 218 RADIATION WINDOW, 219 ROTATION AXIS, 220 CONTAINER, 300 CHANGE AMOUNT MEASUREMENT UNIT, 310-1 AND 310-2 X-RAY DETECTION ELEMENT, 311 SLIT, 312 SUBSTRATE, 70 ANOMALY DETECTION UNIT, 71 CHANGE AMOUNT RECORDING UNIT, 72 COMPARISON UNIT, 73 DISPLAY CONTROL UNIT, 80 ABNORMAL LOCATION SPECIFYING UNIT, 1000 SERVICE LIFE ESTIMATION UNIT, 1200 COMPONENT SEPARATING UNIT, 1400 MONITORING SERVER, 2 CPU, 3 MAIN MEMORY, 4 STORAGE DEVICE, 5 DISPLAY MEMORY, 6 DISPLAY DEVICE, 7 CONTROLLER, 8 MOUSE, 9 KEYBOARD, 10 NETWORK ADAPTOR, 11 SYSTEM BUS, 12 NETWORK, 13A TO 13D X-RAY DIAGNOSTIC IMAGING APPARATUS

The invention claimed is:
1. An X-ray diagnostic imaging apparatus comprising:
an X-ray tube that irradiates an object with X-rays;

an X-ray detector that detects X-rays having been transmitted through the object;

an image creation unit that creates a medical image of the object on the basis of the output of the X-ray detector;

a change amount measurement unit that measures a change amount of an X-ray focal point which is an X-ray generation point of the X-ray tube; and an anomaly detection unit that detects an anomaly in the X-ray tube on the basis of whether or not the change amount falls within a predetermined normal change range, wherein the anomaly detection unit includes a comparison unit that compares the change amount with the normal change range correlated with scanning conditions when the change amount is measured, so as to determine the presence or absence of an anomaly in the X-ray tube.

2. The X-ray diagnostic imaging apparatus according to claim 1, further comprising:

a display control unit that receives a determination result of whether the X-ray tube is normal or abnormal from the comparison unit, and displays the determination result on a display device.

3. The X-ray diagnostic imaging apparatus according to claim 1, wherein the anomaly detection unit further includes a change amount recording unit that records the change amount and scanning conditions when the change amount is measured in correlation with each other.

4. The X-ray diagnostic imaging apparatus according to claim 1, further comprising:

a storage unit that stores the normal change range in correlation with scanning conditions.

5. The X-ray diagnostic imaging apparatus according to claim 1, wherein the anomaly detection unit further includes an abnormal location specifying unit that specifies an abnormal location on the basis of a period in which the change amount falls within an abnormal change range other than the normal change range when the comparison unit determines that there is an anomaly.

6. The X-ray diagnostic imaging apparatus according to claim 5, wherein the abnormal location specifying unit specifies a cathode of the X-ray tube as an abnormal location in a case where a period in which the change amount falls within the abnormal change range is more than a set threshold value.

7. The X-ray diagnostic imaging apparatus according to claim 5, wherein the abnormal location specifying unit specifies a rotation body support of the X-ray tube as an abnormal location in a case where the change amount vibrates between the normal change range and the abnormal change range.

8. The X-ray diagnostic imaging apparatus according to claim 1, further comprising:

a service life estimation unit that estimates the service life of the X-ray tube on the basis of a vibration amount of the X-ray focal point.

9. The X-ray diagnostic imaging apparatus according to claim 3, further comprising:

a rotation disk that is mounted with the X-ray tube and the X-ray detector, wherein the anomaly detection unit further includes a component separating unit that separates the change amount recorded in correlation with the scanning conditions by the change amount recording unit into a thermal expansion component related to thermal expansion and a centrifugal force component related to centrifugal force.

10. The X-ray diagnostic imaging apparatus according to claim 9, wherein the comparison unit acquires the thermal expansion component and the centrifugal force component of the change amount from the component separating unit, and compares each of the thermal expansion component and the centrifugal force component with the normal change range.

11. A monitoring server connected to the X-ray diagnostic imaging apparatus according to claim 1 via a network, wherein the monitoring server receives data regarding the change amount or data regarding an output from the anomaly detection unit from the X-ray diagnostic imaging apparatus, and collectively manages the data.

12. The monitoring server according to claim 11, wherein the service life of the X-ray tube is estimated on the basis of the data, and the replacement time of the X-ray tube is planned and displayed on the basis of the estimated service life.

13. The monitoring server according to claim 11, wherein an abnormal location in the X-ray tube is specified on the basis of the data, and a location to be inspected in the X-ray diagnostic imaging apparatus is presented on the basis of the history of the specified abnormal location.

14. An anomaly detection method of detecting an anomaly in an X-ray diagnostic imaging apparatus including an X-ray tube that irradiates an object with X-rays, an X-ray detector that detects X-rays having been transmitted through the object, and an image creation unit that creates a medical image of the object on the basis of the output of the X-ray detector, the method comprising:

a measurement step of measuring a change amount of an X-ray focal point which is an X-ray generation point of the X-ray tube; and an anomaly detection step of detecting an anomaly in the X-ray tube on the basis of whether or not the change amount falls within a predetermined normal change range, wherein the anomaly detection step includes a comparison step of comparing the change amount with the normal change range correlated with scanning conditions when the change amount is measured, so as to determine the presence or absence of an anomaly in the X-ray tube.

* * * * *